US007960114B2

(12) United States Patent
Seigneuric et al.

(10) Patent No.: US 7,960,114 B2
(45) Date of Patent: Jun. 14, 2011

(54) GENE SIGNATURE OF EARLY HYPOXIA TO PREDICT PATIENT SURVIVAL (75) Inventors: Renaud G. Seigneuric, Crimolois (FR); Maud H. W. Starmans, Heerlen (NL); Glenn Fung, Madison, WI (US); Balaji Krishnapuram, King of Prussia, PA (US); Dimitry S. A. Nuyten, Branford, CT (US); Arie van Erk, Eindhoven (NL); Michael Gaston Magagnin, Riemst (BE); Kasper M. Rouschop, Wijnandsrade (NL); Sriram Krishnan, Exton, PA (US); R. Bharat Rao, Berwyn, PA (US); Christoffel Theodorus Anthonius Evelo, Geleen (NL); Adrian Campbell Begg, Amsterdam (NL); Bradly G. Wouters, Toronto (CA); Philippe Lambin, Genappe-Bousval (BE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 140 days.

(21) Appl. No.: 12/113,373

(22) Filed: May 1, 2008

(65) Prior Publication Data
US 2009/0130096 A1 May 21, 2009

Related U.S. Application Data (60) Provisional application No. 60/915,531, filed on May 2, 2007.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| 7,421,417 B2 | 9/2008 | Mangasarian et al. |
| 2007/0021918 A1 | 1/2007 | Natsoulis et al. |

FOREIGN PATENT DOCUMENTS

| WO | 2006/119593 A | 11/2006 |
| WO | 2008/037700 A | 4/2008 |
| WO | 2008/094678 A | 8/2008 |

OTHER PUBLICATIONS

NCBI, "UniGene entry Hs.596783 has been retired," printed Mar. 2010, one page.*
Sorlie et al (PNAS, 2001, 98:10869-10874).*
Chi et al (PLoS medicine, Mar. 2006, 3:395-409).*
Sorlie et al, 2001, Supplemental Figure 5.*
Sorlie et al, 2001, Supplemental Figure 7.*
Sorlie et al, 2001, Supplemental Figure 8.*
Tockman et al (Cancer Res., 1992, 52:2711s-2718s).*
Bi, J., Bennett, K., Embrechts, M., Breneman, C. & Song, M. "Dimensionality reduction via sparse support vector machines" Journal of Machine Learning Research 3, 1229-1243 (2003).
David G. Kleinbaum and J. Klein, "Statistics for Biology and Health—A Self-Learning Text", Springer, Second Edition, 2003; pp. 45-82.
Span et al., "Carbonic anhydrase-9 expression levels and prognosis in human breast cancer: Association with treatment outcome", British Journal of Cancer, vol. 89, No. 2, Jul. 21, 2003, pp. 271-276.
Trastour et al., "HIF-1 alpha and CA IX staining in invasive breast carcinomas: Prognosis and treatment outcome", International Journal of Cancer, John Wiley & Sons, Inc, US, Switzerland, Germany, vol. 120, No. 7, Apr. 1, 2007, pp. 1451-1458.
Lal et al., "Transcriptional response to hypoxia in human tumors", Journal of the National Cancer Institute (Bethesda), vol. 93, No. 17, Sep. 5, 2001, pp. 1337-1343.
Wang et al., "Gene selection for microarray data analysis using principal component analysis", Statistics in Medicine, vol. 24, No. 13, Jul. 2005, pp. 2069-2087.
Maokuan et al.", Unlabeled data classification via support vector machines and k-means clustering", Computer Graphics, Imaging and Visualization, 2004, CGIV 2004, Proceedings International Conference on Penang, Malaysia, Jul. 26-29, 2004, IEEE, Piscataway, NJ Jul. 26, 2004, pp. 183-186.
Ataman et al., "Learning to rank by maximizing AUC with linear programming", IJCNN '06, International Joint Conference on Neural Networks, IEEE, Piscataway, NJ, 2006, pp. 123-129.
Starmans et al., "Proliferation and 'invasiveness' gene-expression signatures predict survival of surgically treated non-small-cell lung cancer: D6-03", Journal of Thoracic Oncology, Suppl. 4, vol. 2, No. 8, Aug. 2007, p. S407.
Rosenwald et al., "The proliferation gene expression signature is a quantitative integrator of oncogenic events that predicts survival in mantle cell lymphoma", Cancer Cell, vol. 3, No. 2, Feb. 1, 2003, pp. 185-197.
Whitfield et al., "Common markers of proliferation", Nature Reviews, Cancer Feb. 2006, vol. 6, No. 2, pp. 99-106.
Sotiriou et al., "Comprehensive molecular analysis of several prognostic signatures using molecular indices related to hallmarks of breast cancer: proliferation index appears to be the most significant component of all signatures", Breast Cancer Research and Treatment, vol. 100, No. Suppl. 1, 2006, p. S86.
Desmedt et al., "Proliferation—The most prominent predictor of clinical outcome in breast cancer", Cell Cycle, vol. 5, No. 19, Aug. 1, 2006, pp. 2198-2202.
Rhodes et al., "Large-scale meta-analysis of cancer microarray data identifies common transcriptional profiles of neoplastic transformation and progression", Proceedings of the National Academy of Sciences of USA, National Academy of Science, Washington, DC, vol. 101, No. 25, Jun. 22, 2004, pp. 9309-9314.
International Search Report including Notification of Transmittal of the International Search Report, International Search Report, and Written Opinion of the International Searching Authority.

(Continued)

*Primary Examiner* — Laura B Goddard
(74) *Attorney, Agent, or Firm* — Joshua B. Ryan (57) ABSTRACT

The present invention provides methods and compositions for predicting patient responses to cancer treatment using hypoxia gene signatures. These methods can comprise measuring in a biological sample from a patient the levels of gene expression of a group of the genes designated herein. The present invention also provides for microarrays that can detect expression from a group of genes.

2 Claims, 2 Drawing Sheets

OTHER PUBLICATIONS

Smith, "Neuroprotection against hypoxia-ischemia by insulin-like growth factor-I (IGF-I)", Investigational Drugs Journal; Dec. 2003; vol. 6, No. 12, pp. 1173-1177.

Klein et al., "Statistics for Biology and Health—A Self-Learning Text", Springer, Second Edition, 2003; pp. 45-82.

Bild, A.H., et al., "Linking Oncogenic Pathways with Therapeutic Opportunities", Nat. Rev. Cancer, 2006; 6 (9): 735-41.

Fan, JB, et al., "Highly parallel genomic assays", Nat Rev Genet 2006;7:632-44.

Quackenbush, J., "Microarray Analysis and Tumor Classification", N. Eng. J. of Med., 2006; 354(23): 2463-72.

Han, Z, et al., "Signal transduction network motifs and biological memory", J Theor Biol 2007;246:755-61.

Hood, L, et al., "Systems biology and new technologies enable predictive medicine", Science 2004;306:640-3.

Chang, H.Y., et al., "Gene Expression Signature of Fibroblast Serum Response Predicts Human Cancer Progression: Similarities Between Tumors and Wounds", PLoS Biol., 2004; 2(2):E7.

Chi, J.T., et al., "Gene Expression Programs in Response to Hypoxia: Cell Type Specificity and Prognostic Significance in Human Cancers", PLoS Med., 2006; 3(3):E47.

Palsson, B., "The challenges of in silico biology", Nat Biotechnol 2000;18:1147-50.

Perou, CM, et al., "Molecular portraits of human breast tumours", Nature 2000;406:747-52.

Chang HY, et al., "Robustness, scalability, and integration of a wound-response gene expression signature in predicting breast cancer survival" Proc Natl Acad Sci U S A 2005;102(10):3738-43.

Seigneuric, R, et al., "Impact of supervised gene signatures of early hypoxia on patient survival", Rad. Oncol 2007.

van de Vijver MJ, et al., "A gene-expression signature as a predictor of survival in breast cancer", N Engl. J Med 2002; 347(25):1999-2009.

Semenza, GL., "Targeting HIF-1 for cancer therapy", Nat Rev Cancer 2003;3:721-32.

Vogelstein, B., et al., "Surfing the p53 network", Nature 2000;408:307-10.

West, M, et al., "Embracing the complexity of genomic data for personalized medicine", Genome Res 2006;16:559-66.

Ramaswamy, S, et al., "Multiclass cancer diagnosis using tumor gene expression signatures", Proc Natl Acad Sci U S A 2001;98:15149-54.

Wouters, BG., et al., "Targeting hypoxia tolerance in cancer", Drug Resist Updat 2004;7:25-40.

I. Guyon, et al., "Gene selection for cancer classification using support vector machines", Machine Learning 2002;46,1-3, 389-422.

M. Schmidt, et al., "Fast optimization methods for L1 regularization: A comparatve study and two new approaches" To be published in the ECML 2007 proceedings (http://pages.cs.wisc.edu/~gfung/GeneralL1/).

S. Agarwal, et al., "Leaning to Rank", Procedings of the NIPS 2005 workshop. 2005.

G. Fung, et al., "Learning rankins via convex hull separations", NIPS 18 2006.

R. Rosales, et al., "Learning sparse metrics via linear programming", Procedings of the 2006 conference on Knowledge Discovery and Data Mining (KDD 2006). 2006.

Miller LD, et al., "An expression signature for p53 status in human breast cancer predicts mutation status, transcriptional effects, and patient survival", Proc Natl. Acad. Sci. U S A 2005; 102(38):13550-5.

Fung, G., et al., "Reducing a biomarkers list via mathematical programming: application to gene signatures to detect time-dependent hypoxia in cancer".

Bussink, J., et al., "Microenvironmental transformations by VEGF- and EGF-receptor inhibition and potential implications for responsiveness to radiotherapy", Radiother. Oncol., 2007; 82: 10-7.

Chung, C.H., et al., "Molecular portraits and the family tree of cancer", Net. Genet., 2002; 32 Suppl.: 533-40.

van 't Veer LJ, et al., "Gene expression profiling predicts clinical outcome of breast cancer", Nature 2002; 415(6871):530-6.

Denko, N.C., et al., "Investigating hypoxic tumor physiology through gene expression patterns", Oncogene, 2003; 22: 5907-14.

Eisen, et al., "Cluster analysis and display of genome-wide expression patterns", Proc. Natl. Acad. Sci. USA, 1998; 95:14863-8.

Eriksen, et al., "Tumour hypoxia—a characteristic feature with a complex molecular background", Radiother. Oncol., 2006; 81:119-21.

Huang, et al., "Gene expression phenotypes of oncogenic signaling pathways", Cell Cycle, 2003; 2:415-7.

Iyer, et al., "The transcriptional program in the response of human fibroblasts to serum", Science, 1999: 283:83-7.

Kietzmann, et al., "Signaling cross-talk between hypoxia and glucose via hypoxia-inducible factor 1 and glucose response elements", Biochem. Pharmacol., 2002; 64:903-11.

Koritzinsky, et al., "The hypoxic proteome is influenced by gene-specific changes in mRNA translation", Radiother. Oncol., 2005; 76:177-86.

Riedemann, et al., "IGF1R signaling and its inhibition", Endocr. Relat. Cancer, 2006; 13 Suppl.:S33-43.

Sjogren, et al., "The p53 gene in breast cancer" prognostic value of complementary DNA sequencing versus immunohistochemistry, J. of Natl. Cancer Inst., 1996; 88:173-82.

Sorenson, et al., "Influence of oxygen concentration and pH on expression of hypoxia induced genes", Radiother. Oncol., 2005; 76:187-93.

Troost, et al., Imaging hypoxia after oxygenation-modification: comparing [18F]FMISO autoradiography with pimonidazole immunohistochemistry in human xenograft tumors, Radiother. Oncol., 2006; 80:157-64.

Vaupel, P., "The role of hypoxia-induced factors in tumor progression", Oncologist, 2004; 9 Suppl. 5:10-7.

* cited by examiner

GENE SIGNATURE OF EARLY HYPOXIA TO PREDICT PATIENT SURVIVAL

CROSS-REFERENCE TO RELATED APPLICATION

The present patent document claims the benefit of the filing date under 35 U.S.C. §119(e) of Provisional U.S. Patent Application Ser. No. 60/915,531, filed May 2, 2007, which is hereby incorporated by reference.

BACKGROUND

Field of the Invention

Maintenance of physiological oxygen concentrations is a highly dynamic process vital to many aspects of cell biology. Lack of oxygen (hypoxia) is a frequently encountered situation in solid tumors and is associated with increased radiotherapy and chemotherapy resistance, malignancy and poor prognosis (2, 8, 18, 19, 22, and 23). Hypoxia is known to be highly heterogeneous within tumors in terms of its spatial distribution, severity and kinetics. Hypoxia arises through different mechanisms associated primarily with limits in oxygen diffusion (chronic hypoxia) and blood perfusion (acute hypoxia). In addition, hypoxia regulates several different cellular pathways that have unique activation kinetics and sensitivity to oxygen concentration. As a consequence, hypoxia regulated gene expression is complex and displays large temporal characteristics.

With DNA microarrays, it is now possible to monitor the expression of several tens of thousands of genes at once. In oncology, this ability is exploited to extract lists of genes (or gene signatures) rather than to rely on a few clinical variables for diagnosis (5, 14) or prognosis. For the latter, these gene sets include those derived from clinical data, in which correlation with a supervised classifier identifies the clinical group with a better or worse prognosis (13, 20, 21). More recently, in vitro derived gene sets have been described containing genes associated with a particular phenotype hypothesized to be clinically important (1, 3, 4, 9). This allows an unbiased test of such a hypothesis, by applying the in vitro derived signature to a separate patient microarray study. This latter type of study recently demonstrated that a gene signature for hypoxia could act as a prognostic factor in a range of different tumor types. In this latter study, Chi et al. (4) also measured the temporal gene expression programs under hypoxia for several primary cell lines in vitro. The Chi et al. dataset might be used to extract hypoxic gene signatures that reflect differences between slow and fast hypoxia kinetic responses and their contribution to prognosis because of the large dependency of hypoxic gene expression on time. In view of the above, it is apparent that there exists a need for improved hypoxic gene signatures for the identification, diagnosis, and treatment of cancer.

SUMMARY

In one aspect, the present invention provides for methods for predicting patient response to cancer treatment comprising measuring in a biological sample from a patient the levels of gene expression of a plurality of genes selected from the groups consisting of Group A, B, and C, defined below: a. Group A: Genes corresponding to transcripts associated with the Unigene ID Nos. Hs.592692, Hs.633514, Hs.127126, Hs.334587, Hs.648626, Hs.646346, Hs.584803, Hs.567495, Hs.651126, Hs.478746, Hs.72550, Hs.154276, Hs.233568, Hs.106861, Hs.414-418, Hs.593565, Hs.235116, Hs.554791, Hs.226780, Hs.525549, Hs.536158, Hs.438-489, Hs.643279, Hs.189772, Hs.78977, Hs.155983, Hs.612872, Hs.435933, Hs.489603, Hs.128959, Hs.335205, Hs.146406, Hs.596783, Hs.512973, Hs.461030, Hs.149983, Hs.464137, Hs.292524, Hs.283749, Hs.287362, Hs.492203, Hs.250693, Hs.593232, Hs.590575, Hs.428214, Hs.523847, Hs.533712, Hs.44067, Hs.647072, Hs.606472, Hs.149032, Hs.436705, Hs.631539, Hs.529353, Hs.592020, Hs.642938, Hs.631930, Hs.148907, Hs.160556, Hs.126891, Hs.124011, Hs.524828, Hs.4779, Hs.612872, Hs.233240, Hs.445030, Hs.460, Hs.112432, Hs.544738, Hs.530941, Hs.180903, Hs.76364, Hs.43627, Hs.643599, Hs.125038, Hs.131342, Hs.512767, Hs.631974, Hs.112873, and Hs.6217; b. Group B: Genes corresponding to transcripts associated with the Unigene ID Nos. Hs.72550, Hs.528299, Hs.510078, Hs.633514, Hs.602706, Hs.642877, Hs.593232, Hs.596783, Hs.441113, Hs.149983, Hs.94542, Hs.154276, Hs.189772, Hs.112432, Hs.643599, Hs.126774, Hs.146406, Hs.463838, Hs.523847, Hs.46700, Hs.55131, Hs.558396, Hs.148907, Hs.643920, Hs.160556, Hs.562083, Hs.515383, Hs.513430, Hs.155983, Hs.590575, Hs.632226, Hs.165607, Hs.514033, Hs.632447, Hs.89603, and Hs.434961; and c. Group C: Genes corresponding to transcripts associated with the Unigene ID Nos. Hs.72550, Hs.633514, Hs.593232, Hs.596783, Hs.149983, Hs.154276, Hs.189772, Hs.112432, Hs.643599, Hs.146406, Hs.523847, Hs.148907, Hs.160556, Hs.155983, and Hs.590575; and creating a signature score from said levels of gene expression; and correlating the signature score with a predicted response to cancer treatment.

In certain embodiments, the levels of gene expression are measured by determining the levels of expression of a group of polynucleotide sequences selected from the group consisting of: d. the sequences SEQ ID NOS: 1-80; e. the sequences SEQ ID NOS: 11, 81, 82, 2, 83, 84, 43, 33, 85, 36, 86, 12, 24, 68, 74, 87, 32, 88, 46, 89, 90, 91, 58, 92, 59, 93, 94, 95, 26, 44, 96, 97, 98, 99, 100, and 101; and f. the sequences SEQ ID NOS: 11, 2, 43, 33, 36, 12, 24, 68, 74, 32, 46, 58, 59, 26, and 44. In particular embodiments, the cancer is breast, renal, or lung cancer. In certain embodiments, the measuring of the levels of gene expression is carried out on RNA from said biological sample. The biological sample in particular embodiments is from a tumor, a cancerous tissue, a pre-cancerous tissue, a biopsy, a tissue, lymph node, a surgical excision, blood, serum, urine, an organ, or saliva. The treatment of the cancer may comprise radiotherapy, fractionated radiotherapy, chemotherapy, or chemo-radiotherapy in particular embodiments.

In a second aspect, the present invention provides for microarrays comprising: a solid substrate and a plurality of nucleic acid probes capable of detecting the levels of gene expression of a plurality of genes selected from the groups consisting of Group A, B, and C, defined below: a. Group A: Genes corresponding to transcripts associated with the Unigene ID Nos. Hs.592692, Hs.633514, Hs.127126, Hs.334587, Hs.648626, Hs.646346, Hs.584803, Hs.567495, Hs.651126, Hs.478746, Hs.72550, Hs.154276, Hs.233568, Hs.106861, Hs.414-418, Hs.593565, Hs.235116, Hs.554791, Hs.226780, Hs.525549, Hs.536158, Hs.438-489, Hs.643279, Hs.189772, Hs.78977, Hs.155983, Hs.612872, Hs.435933, Hs.489603, Hs.128959, Hs.335205, Hs.146406, Hs.596783, Hs.512973, Hs.461030, Hs.149983, Hs.464137, Hs.292524, Hs.283749, Hs.287362, Hs.492203, Hs.250693, Hs.593232, Hs.590575, Hs.428214, Hs.523847, Hs.533712, Hs.44067, Hs.647072, Hs.606472, Hs.149032, Hs.436705, Hs.631539, Hs.529353, Hs.592020, Hs.642938, Hs.631930, Hs.148907, Hs.160556, Hs.126891, Hs.124011, Hs.524828, Hs.4779, Hs.612872, Hs.233240, Hs.445030, Hs.460, Hs.112432, Hs.544738, Hs.530941, Hs.180903, Hs.76364, Hs.43627, Hs.643599, Hs.125038, Hs.131342, Hs.512767, Hs.631974, Hs.112873, and Hs.6217; b. Group B: Genes corresponding to transcripts associated with the Unigene ID Nos. Hs.72550, Hs.528299, Hs.510078, Hs.633514, Hs.602706, Hs.642877, Hs.593232, Hs.596783, Hs.441113, Hs.149983, Hs.94542, Hs.154276, Hs.189772, Hs.112432, Hs.643599, Hs.126774, Hs.146406, Hs.463838, Hs.523847, Hs.46700, Hs.55131, Hs.558396, Hs.148907, Hs.643920, Hs.160556, Hs.562083, Hs.515383, Hs.513430, Hs.155983, Hs.590575, Hs.632226, Hs.165607, Hs.514033, Hs.632447, Hs.89603, and Hs.434961; and c. Group C: Genes corresponding to transcripts associated with the Unigene ID Nos. Hs.72550, Hs.633514, Hs.593232, Hs.596783, Hs.149983, Hs.154276, Hs.189772, Hs.112432, Hs.643599, Hs.146406, Hs.523847, Hs.148907, Hs.160556, Hs.155983, and Hs.590575. In particular embodiments, the microarray contains a plurality of nucleic acid probes are capable of detecting the expression of a group of sequences selected from the group consisting of: d. the sequences SEQ ID NOS: 1-80; e. the sequences SEQ ID NOS: 11, 81, 82, 2, 83, 84, 43, 33, 85, 36, 86, 12, 24, 68, 74, 87, 32, 88, 46, 89, 90, 91, 58, 92, 59, 93, 94, 95, 26, 44, 96, 97, 98, 99, 100, and 101; and f. the sequences SEQ ID NOS: 11, 2, 43, 33, 36, 12, 24, 68, 74, 32, 46, 58, 59, 26, and 44. In particular embodiments, the plurality of probes comprise DNA sequences. The plurality of probes are capable of hybridizing to the sequences of at least one of the groups (d)-(f) under the hybridization conditions of 6×SSC at 65° C., in certain embodiments. In certain embodiments, the plurality of probes comprise from about 15 to 50 base pairs of DNA.

In a third aspect, the present invention provides for kits comprising a microarray comprising a plurality of nucleic acid probes capable of detecting the expression of a group of sequences selected from the group consisting of: groups (d)-(f) described above; and directions for us of the kit.

In a fourth aspect, the present invention provides for methods of treating cancer comprising measuring in a biological sample from a patient the levels of gene expression of a plurality of genes selected from the groups consisting of Group A, B, and C, defined below: a. Group A: Genes corresponding to transcripts associated with the Unigene ID Nos. Hs.592692, Hs.633514, Hs.127126, Hs.334587, Hs.648626, Hs.646346, Hs.584803, Hs.567495, Hs.651126, Hs.478746, Hs.72550, Hs.154276, Hs.233568, Hs.106861, Hs.414-418, Hs.593565, Hs.235116, Hs.554791, Hs.226780, Hs.525549, Hs.536158, Hs.438-489, Hs.643279, Hs.189772, Hs.78977, Hs.155983, Hs.612872, Hs.435933, Hs.489603, Hs.128959, Hs.335205, Hs.146406, Hs.596783, Hs.512973, Hs.461030, Hs.149983, Hs.464137, Hs.292524, Hs.283749, Hs.287362, Hs.492203, Hs.250693, Hs.593232, Hs.590575, Hs.428214, Hs.523847, Hs.533712, Hs.44067, Hs.647072, Hs.606472, Hs.149032, Hs.436705, Hs.631539, Hs.529353, Hs.592020, Hs.642938, Hs.631930, Hs.148907, Hs.160556, Hs.126891, Hs.124011, Hs.524828, Hs.4779, Hs.612872, Hs.233240, Hs.445030, Hs.460, Hs.112432, Hs.544738, Hs.530941, Hs.180903, Hs.76364, Hs.43627, Hs.643599, Hs.125038, Hs.131342, Hs.512767, Hs.631974, Hs.112873, and Hs.6217; b. Group B: Genes corresponding to transcripts associated with the Unigene ID Nos. Hs.72550, Hs.528299, Hs.510078, Hs.633514, Hs.602706, Hs.642877, Hs.593232, Hs.596783, Hs.441113, Hs.149983, Hs.94542, Hs.154276, Hs.189772, Hs.112432, Hs.643599, Hs.126774, Hs.146406, Hs.463838, Hs.523847, Hs.46700, Hs.55131, Hs.558396, Hs.148907, Hs.643920, Hs.160556, Hs.562083, Hs.515383, Hs.513430, Hs.155983, Hs.590575, Hs.632226, Hs.165607, Hs.514033, Hs.632447, Hs.89603, and Hs.434961; and c. Group C: Genes corresponding to transcripts associated with the Unigene ID Nos. Hs.72550, Hs.633514, Hs.593232, Hs.596783, Hs.149983, Hs.154276, Hs.189772, Hs.112432, Hs.643599, Hs.146406, Hs.523847, Hs.148907, Hs.160556, Hs.155983, and Hs.590575; and administering a therapeutically effective amount of one or more cancer treatment agents selected from the group consisting of: cancer chemotherapeutic agents and radiation; or performing surgery on the patient; or a combination thereof. In further embodiments, the levels of gene expression are measured by determining the levels of expression of a group of polynucleotide sequences selected from the group consisting of groups (d)-(f) described above.

In certain embodiments, the one or more cancer treatment agents are selected from the group consisting of: paclitaxel, docetaxel, imatinib mesylate, sunitinib malate, cisplatin, etoposide, vinblastine, methotrexate, adriamycin, cyclophosphamide, doxorubicin, daunomycin, 5-fluoruracil, vincristine, endostatin, angiostatin, bevacizumab, and rituximab. In another embodiment, the one or more cancer treatment agents is radiation. In particular embodiments, the cancer being treated is breast, renal, or lung cancer. In certain embodiments, the methods of treatment comprise surgery.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

FIG. 1 depicts Kaplan-Meier survival curves for disease specific survival (follow-up to 12 years) and p-values for different gene signatures. For the groups in A, B, C and (left-hand top and bottom panels), the group with the low expression is the top curve, the group with the high expression is the bottom curve. For the groups in C (right-hand top panel and right-hand bottom panel), the group with the high expression is the top curve, the group with the low expression is the bottom curve. Panel A is the (A) Chi signature (8). Panel B are the early hypoxia (under 0 or 2%), signatures. Panel (C) are the late signatures. A signature score was calculated for each patient in the different datasets. These scores were used to cluster the patients in two groups, one with low expression and one with high expression of the signature. Kaplan-Meier survival curves for the two groups were compared. Patients with tumors with a high proliferation signature score had worse outcomes than those with tumors with a low proliferation signature score.

DETAILED DESCRIPTION

Figure 1A:
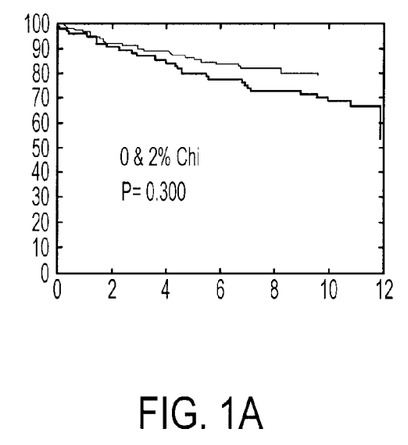
Figure 1B:
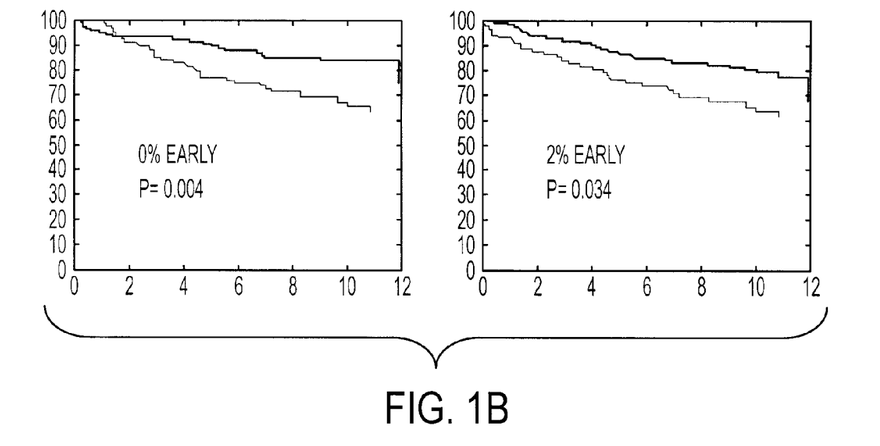
Figure 1C:
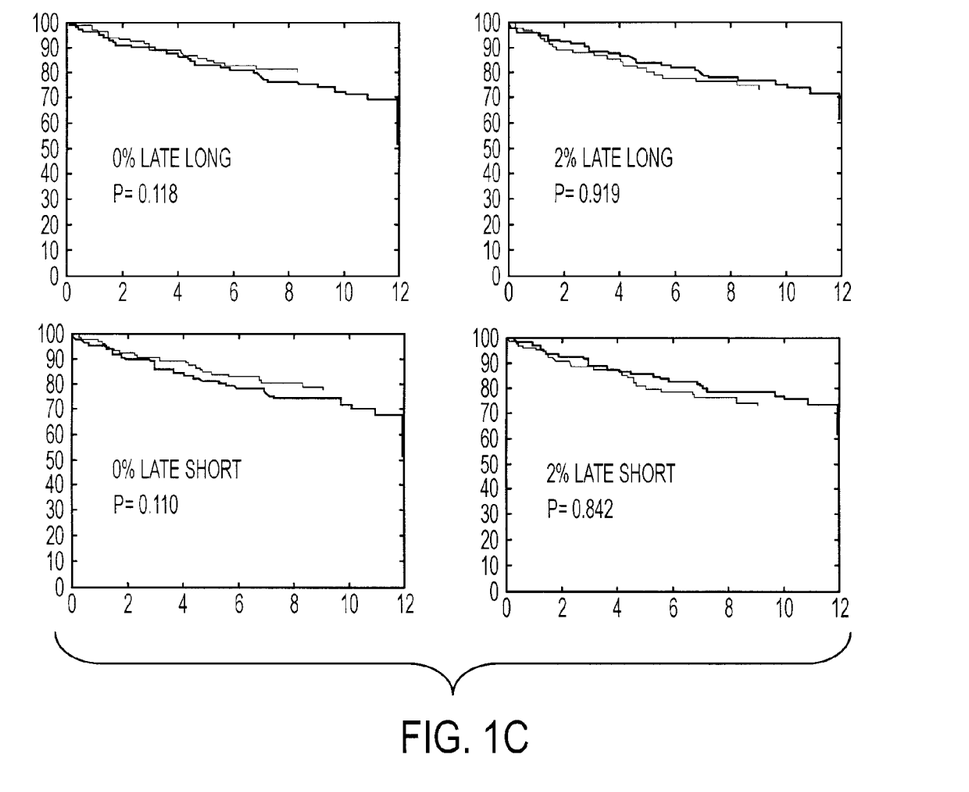

Hypoxia is a common feature of solid tumors associated with therapy resistance, increased malignancy and poor prognosis. Several approaches have been developed with the hope of identifying patients harboring hypoxic tumors including the use of microarray based gene signatures. However, studies to date have largely ignored the strong time dependency of hypoxia regulated gene expression. It is hypothesized that use of time-dependent patterns of gene expression during hypoxia would enable development of superior prognostic expression signatures.

The present invention provides methods and compositions for predicting patient response to cancer treatment using gene signatures. The methods typically involve measuring in a biological sample from a patient the levels of gene expression of a group of the genes corresponding to transcripts associated with a particular groups of Unigene ID Nos. In particular embodiments, the Unigene ID Nos. are selected from groups (a)-(c) as set out above. One Unigene ID No. may have multiple transcripts associated with it. Examples of a DNA sequence associated with each Unigene ID No. of groups (a) may be found in Table 2A as SEQ ID NOS. 1-80.

To examine the levels of gene expression of one or more sequences or Unigene ID Nos., a biological sample of a patient that is suffering from a cancer or who has yet to be diagnosed with cancer is typically assayed. A "biological sample" includes a sample from a tumor, cancerous tissue, pre-cancerous tissue, biopsy, tissue, lymph node, surgical excision, blood, serum, urine, organ, saliva, etc. obtained from a patient suffering from a cancer or who has yet to be diagnosed with cancer.

The biological sample is then typically assayed from the presence of one or more gene expression products such as RNA, cDNA, cRNA, protein, etc.

In one embodiment, mRNA from a biological sample is directly used in determining the levels of expression of a group of genes. In one particular embodiment, RNA is obtained from a biological sample. The RNA is then transformed into cDNA (complementary DNA) copy using methods known in the art. In particular embodiments, the cDNA is labeled with a fluorescent label or other detectable label. The cDNA is then hybridized to a substrate containing a plurality of probes of interest. A probe of interest typically hybridizes under stringent hybridization conditions to at least one DNA sequence of a gene signature. In certain embodiments, the plurality of probes are capable of hybridizing to the sequences of at least one of the group of DNA sequences of groups (d)-(f) under the hybridization conditions of 6×SSC (0.9 M NaCl, 0.09 M sodium citrate, pH 7.4) at 65° C. The probes may comprise nucleic acids. An example of a nucleic acid is DNA. The term "nucleic acid" refers to deoxyribonucleotides or ribonucleotides and polymers thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, peptide-nucleic acids (PNAs).

In certain cases, the probes will be from about 15 to about 50 base pairs in length. The amount of cDNA hybridization can be measured by assaying for the presence of the detectable label, such as a fluorophore. The quantification of the hybridization signal can be used to generate a score for a particular sequence or set of sequences in the gene signature for a particular patient or plurality of patients.

The term "detectable label" refers to a moiety that is attached through covalent or non-covalent means to an entity being measured or a probe. A "detectable label" can be a radioactive moiety, a fluorescent moiety, a chemiluminescent moiety, etc. The term "fluorescent label" refers to label that accepts radiant energy of one wavelength and emits radiant energy of a second wavelength. The presence of a detectable label may be assayed using methods known in the art that are appropriate to detect a particular label, such as spectrophotometric means (e.g., a spectrophotometer), radiometric means (e.g., scintillation counter), fluorometer, luminometer, etc.

Included within the scope of the invention are DNA microarrays containing a plurality of sequences that hybridize under stringent hybridization conditions to one or more of the gene sequences in a gene signature. An example of a substrate containing one or more probes of interest is a plurality of DNA probes that are affixed to a substrate. In certain embodiments, the substrate may comprise one or more materials such as gel, nitrocellulose, nylon, quartz, glass, metal, silica based materials, silica, resins, polymers, etc., or combinations thereof. Typically, the DNA probes comprise about 10-50 bp of contiguous DNA. In certain embodiments, the DNA probes are from about 20 to about 50 bp of contiguous DNA. In certain embodiments, the present invention relates to kits which comprising a microarray directions for its use. The kit may comprise a container which comprises one or more microarrays and directions for their use.

The biological sample may also be analyzed for gene expression of one or more genes in a signature using methods that can detect nucleic acids including, but not limited to, PCR (polymerase chain reaction); RT-PCT (reverse transcriptase-polymerase chain reaction); quantitative PCR, etc.

In certain embodiments, the levels of gene expression are measured by detecting the protein expression products of the genes or DNA sequences. The levels of protein products may be measured using methods known in the art including the use of antibodies which specifically bind to a particular protein. These antibodies, including polyclonal or monoclonal antibodies, may be produced using methods that are known in the art. These antibodies may also be coupled to a solid substrate to form an antibody chip or antibody microarray. Antibody or protein microarrays may be made using methods that are known in the art.

Once the levels of gene expression have been measured then a signature score is created. Examples of how to create a signature score are described herein. The signature score is then correlated with a predicted response to cancer treatment. Typically, a Kaplan-Meier curve may be generated to determine if the signature score is associated with a higher or lower survival rate. In particular embodiments, a positive or negative numerical weight may be assigned to a sequence or Unigene ID No. in the creation of a signature score. If the signature score is associated with a lower survival rate, then aggressive cancer treatment may be indicated. If the signature score is associated with a higher survival rate then less aggressive cancer treatment may be indicated.

The treatment of cancer in certain embodiments, involves measuring the levels of gene expression of a group of Unigene ID Nos. selected from the group consisting of groups (a)-(c). The method of treatment typically further comprises administering a therapeutically effective amount of one or more cancer treatment agents selected from the group consisting of: cancer chemotherapeutic agents and radiation. The treatment of cancer may also comprise surgery or surgical procedures. The treatment of cancer may further comprise surgery and administering a therapeutically effective amount of one or more cancer treatment agents selected from the group consisting of: cancer chemotherapeutic agents and radiation. The term "administering" refers to the method of contacting a compound with a subject. Modes of "administering" may include but are not limited to, methods that involve contacting the cancer chemotherapeutic agents intravenously, intraperitoneally, intranasally, transdermally, topically, via implantation, subcutaneously, parentally, intramuscularly, orally, systemically, and via adsorption. The term "treatment" includes the acute or prophylactic diminishment or alleviation of at least one symptom or characteristic associated or caused by the cancer being treated. For example, treatment can include diminishment of several symptoms of a cancer or complete eradication of a cancer. The phrase "therapeutically effective amount" means an amount of a cancer chemotherapeutic agent, or a pharmaceutically acceptable salt thereof, that is sufficient to inhibit, halt, or allow an improvement in the cancer being treated when administered alone or in conjunction with another pharmaceutical agent or treatment in a particular subject or subject population. For example in a human a therapeutically effective amount can be determined experimentally in a clinical setting, for the particular disease and subject being treated. It should be appreciated that determination of proper dosage forms, dosage amounts and routes of administration is within the level of ordinary skill in the pharmaceutical and medical arts.

It is within the purview of the skill medical practitioner to select an appropriate therapeutic regimen. Therapeutic regimens may be comprised of the use of cancer chemotherapeutic agents and/or radiation. A cancer chemotherapeutic agent is a chemical or biological agent (e.g., antibody, protein, RNA, DNA, etc.) that retards, slows, or stops the growth of cancer or is approved to treat cancer by the U.S. Food and Drug Administration. Examples of cancer chemotherapeutic agents include, but are not limited to: paclitaxel, docetaxel, imatinib mesylate, sunitinib malate, cisplatin, etoposide, vinblastine, methotrexate, adriamycin, cyclophosphamide, doxorubicin, daunomycin, 5-fluoruracil, vincristine, endostatin, angiostatin, bevacizumab, and rituximab. Another example of a cancer treatment agent is radiation. Thus, the cancer treatment may comprise radiotherapy, fractionated radiotherapy, chemotherapy, or chemo-radiotherapy (a combination of one or more chemotherapeutic agents and radiation). The cancer may be any type of cancer. In certain embodiments, the cancer is breast, renal, or lung cancer. Examples of cancer include, but are not limited to: small cell lung cancer, squamous cell lung carcinoma, glioma, breast cancer, prostate cancer, ovarian cancer, cervical cancer, gliobastoma, endometrial carcinoma, heptocellular carcinoma, colon cancer, lung cancer, melanoma, renal cell carcinoma, renal cancer, thyroid carcinoma, squamous cell lung carcinoma, leukemia, cell lymphoma, and lymphoproliferative disorders.

EXAMPLES

Material and Methods

Using published data from the microarray study of Chi et al. (4) gene signatures were extracted correlating with induction during either early or late hypoxic exposure. Gene signatures were derived from in vitro exposed human mammary epithelial cell line (HMEC) under 0% or 2% oxygen. Gene signatures correlating with early and late upregulation were tested by means of Kaplan-Meier survival, univariate, and multivariate analysis on a patient dataset with primary breast cancer treated conventionally (surgery plus on indication radiotherapy and systemic therapy).

Results

Two early hypoxia gene signatures extracted from 0 and 2% hypoxia showed significant prognostic power (log-rank test: p=0.004 at 0%, and p=0.034 at 2%) in contrast to the late hypoxia signatures. Both early gene signatures were linked to the insulin pathway. From the multivariate Cox-regression analysis the early hypoxia signature (p=0.254) was found to be the fourth best prognostic factor after lymph node status (p=0.002), tumor size (p=0.016) and Elston grade (p=0.111). On this data set it indeed provided more information than ER (estrogen receptor) status or p53 status.

Conclusions

The hypoxic stress elicits a wide panel of temporal responses corresponding to different biological pathways. Early hypoxia signatures were shown to have a significant prognostic power. These data suggest that gene signatures identified from in vitro experiments could contribute to individualized medicine.

Material and Methods

Data Set

The starting material was the data set provided by the study of Chi et al. which represents, one of the largest set of time series under hypoxia with 2.4 million of gene expression measurements. Four normal cell lines were used: human coronary artery endothelial cells (ECs), smooth muscle cells (SMCs), human mammary epithelial cells (HMECs), and renal proximal tubule epithelial cells (RPTECs 1 and 2) under 2 oxygen concentrations (less than 0.02% (referred to herein as "0%), and 2%). Using cDNA microarrays of 42,000 reporters, gene expression was monitored under hypoxia resulting in 10 time series with at most 6 time points for each. After Chi et al. filtered for noise and intensity, the time series of the remaining 4,333 reporters was plotted (data now shown)). SM and HMEC both had the longest time series. i.e., six time points: 0, 1, 3, 6, 12, and 24 hours of hypoxia, each for two oxygen concentrations (less than 0.02% (referred to herein as "0%), and 2%). The absence of early time points did not allow for the inclusion of the other cell lines. As also found by Chi et al. it was not possible to clearly define differential expression for the SM cell line due to a low range of expression between up and down regulation. The following analysis thus focuses only on the 2 time series provided for the HMEC cell line: one with an oxygen concentration less than 0.02% (HMEC0), the other under 2% (HMEC2).

A batch query was made with SOURCE to translate the 4,333 CLONEIDs into UniGenes (last accession: February 2007, Build 199). A reporter (probe) was removed if at least one of the following criteria was met: no UniGene identifier was found (328 such reporters); one reporter corresponded to multiple UniGene identifiers (257 such reporters); the Gene Symbol was corresponding to mitochondria (28 such reporters); or the UniGene was not for human (1 such reporter).

For each time series independently, the remaining 3,719 reporters were further filtered out if at least 1 time point was missing. For HMEC0 this resulted in a time series of 1,196 reporters represented by 1,082 unique genes. For the HMEC2 series, it consisted of 1,047 reporters representing 955 unique genes.

Gene Expression Profiling

Extraction of genes with an up-regulation in early time points was assessed in a supervised way. A Pearson correlation was selected as a similarity distance to select profiles based on their time-dependent shape but regardless of their magnitude changes (i.e., an early low or an early high up-regulation are found to be equivalent in these conditions). A curve of interest representing the pattern of gene expression as a function of time was user-defined as a sequence of zeros and ones. The time points 1, 3, and 6 hours were considered early time points in the hypoxia response whereas 12 and 24 hours were reckoned late time points. The curve of interest for selecting genes with an early up-regulation that return back to basal level for late time points was thus set to be 0-111-00. This template was used to select each gene whose temporal profile was similar to this a priori determined pattern of expression. A filtering step was included to require at least a 2 fold induction (with respect to expression under control condition). This procedure was run for each cell line independently. A correlation coefficient of 0.6 was selected to provide gene lists of manageable sizes.

The early hypoxia signature (curve of interest: 0-111-00 for control-early-late time points) was compared to a late hypoxia pattern with a curve of interest being 0-000-11, meaning that gene expression had to be constant and equal to control value during the 3 early time points, then up-regulated at 12 and 24 hours of hypoxia. For each time series, three types of gene signature were derived: early hypoxia; late hypoxia (matching the correlation coefficient (long version); and late hypoxia matching the number of reporters (short version)).

Statistical Analyses

The gene expression based signatures extracted in vitro were evaluated in vivo on a large cancer study providing microarray data (accession number GSE3494). Clinical annotations for its 251 patients (a subset of the Uppsala cohort) with primary breast cancer (Table 1) treated with surgery plus on indication adjuvant radiotherapy and sytemic therapy (13, 16). Expression data was log-transformed and multiple reporters for the same gene symbol were averaged. Depending on the overall expression of the genes selected in the signature, a patient was assigned to either the high expression or the low expression group. Outcome in the two groups was analyzed and compared by the Kaplan-Meier method. Log-rank tests were computed to assess survival differences between the two groups. Univariate and multivariate Cox regression analyses were run with SPSS (SPSS. Chicago. IL.) including all the clinical variables and the early signature under 0%. A machine learning approach was also used to assess the impact of the early signature. It was composed of (1) a feature selection (by leave-one-out cross-validation) followed by (2) a validation stage consisting of a bootstrapping procedure (resampling with replacement) where a randomly picked 70% of the data was used for training and the remaining 30% of the data was used for testing. This procedure was repeated 100 times and the means and standard deviations of the results were reported. Also, multivariate models representing all the possible variable combinations ($2^8-1=255$) were tested and the top 5 performing models were retained.

Results

Correlating genes with a predefined pattern of interest was used to derive early hypoxia gene signatures from the HMEC cell lines under 0% and 2% oxygen. The genes reaching a correlation with the required temporal profile greater than 0.6 and a 2-fold induction or more were selected (Table 2). Results from log-rank tests on the Miller data set were reported in Table 3.

HMEC0%

This number of reporters correlating with early induction (early hypoxia gene signature) following exposure to 0% oxygen was equal to 80 (79 unique UniGenes) (see Table 2A) (signature (a)). For the same level of correlation, 241 reporters (210 unique UniGenes) were found for the late hypoxic signature (late long hypoxic Signature). For comparison, the required correlation was also increased to reduce the number of reporters to match a size similar to the early signature. This late short hypoxic signature contained 74 reporters (70 unique UniGenes) (see Table 2B). Of these three signatures, only the early hypoxia signature was significant on the breast cancer data set (p=0.004 for difference in survival). Surprisingly, the late signatures were not significant and showed no evidence of splitting the patients Into different prognostic groups (p=0.118. p=0.110 for the long and short versions respectively).

HMEC2%

Under 2% oxygen, the number of selected reporters was smaller than under 0% oxygen. The early gene signature contained 36 reporters (36 unique UniGenes) (see Table 2C) (signature (b)) exhibiting an upregulation within the first hours (1-3-6 hours) following hypoxia exposure. The late long hypoxia signature derived with a correlation threshold of 0.6 was made of 169 reporters (147 unique UniGenes). For the short version, the correlation threshold was raised to yield a size comparable to the early one. It was composed of 34 reporters (32 UniGenes) (see Table 2D). Similarly to the results under 0%, the early hypoxia signature was the only significant signature (p=0.034) while the long and short versions of the late hypoxia signature were not (p-value of 0.919 and 0.842 respectively).

Combination of Signatures (0% Oxygen and 2% Oxygen)

Time series without missing data HMEC under 0% oxygen (1,082 UniGenes) and 2% oxygen (955 UniGenes) had a large overlap: 793 UniGenes. Comparing the 2 early signatures revealed a small overlap (15 UniGenes) (see Table 2E) (signature (c)). This core HMEC response was also tested and had a p-value of 0.005 (log-rank test). The overlap between the 2 long late signatures showed an overlap of 93 UniGenes. This core signature for late response was tested and found to be not significant (p=0.240) on the breast cancer dataset.

In order to link the genes from the early signatures to biological functions, Gene Ontologies analyses were ran with Ingenuity Pathways Analysis (Ingenuity Systems, Redwood City, Calif.). The results provided for the top functions are shown in Table 4. For both early signatures, only 2 top functions were found. The genes selected for enrichment ('focus genes') are listed and mainly involved in proliferation, cell cycle, and cancer. For the core early response (intersection of 0 and 2% oxygen), the top function was related to amino acid metabolism.

Prognostic Power of the Early Signature (HMEC0)

A univariate Cox regression analysis was run for the early signature (HMECO) on the Miller data set with all the variables provided and the early hypoxia score. The signature score was found to be significant (p-value<0.05), while progesterone receptor ("PgR") status, estrogen receptor ("ER") status and age were not.

From the multivariate analysis (with a stepbackward feature selection procedure), the early hypoxia signature (p=0.254) was found to be the fourth best prognostic factor after lymph node status (p=0.002), tumor size (p=0.016) and Elston grade (p=0.111). On this data set, it indeed provided more information than ER status or p53 status (both individually and when combined with other variables) for instance.

A multivariate analysis with a machine learning-based feature selection approach was also run. Providing all the variables to the algorithm (but age and the early signature score) gave an Area Under the Curve ("AUC") of 62.3 with a standard deviation (std) of 0.07. Repeating the same analysis but adding age only gave an AUC of 62.2 with a std of 0.07. When age and the signature score were added together, the AUC was 62.5 (std of 0.07). When only the signature score was added, the AUC was 66.1 (std of 0.06). From the hundred runs computed for each analysis, a t-test was performed between the six variables and the signature score versus the six variables and the age. A p-value of 4.8e−6 suggested that age is less effective than the signature score on this data set.

It is also important to note that when all possible variable combinations were considered for training a multivariate model, four out of the top five performing combinations included the signature score.

Discussion

Early Hypoxia

The impact of the early response to hypoxia which with the exception of a few studies (e.g., (12)) is rarely investigated by means of microarrays. Due to potential differences arising for different oxygen concentrations, the 2 time series were treated independently. Both early hypoxia signatures were significant (p<0.01 at 0% oxygen; p<0.05 at 2% oxygen) whereas none of the late signatures were. A signature of the 15 common UniGenes (13 symbols) found in the 2 early signatures was also tested and found to be significant (p=0.005) (See Table 2E).

Ingenuity Pathways Analysis identified genes within this list including ACACA; AMH; BACH1; CCT2 (related to growth and apoptosis) and IFI6 in Cancer, Tumor Morphology, and Amino Acid Metabolism (Table 4). Focusing on the early signature at 0% oxygen (p=0.004) with Ingenuity Pathways Analysis revealed a significant contribution of IGF1R (from the canonical insulin pathway); TERT (Telomerase reverse transcriptase); AMH; COL6A3; and ACACA in apoptosis, growth, and proliferation. CCNH (from the estrogen receptor pathway) as well as transcription factors ATF3 and BACH1 were also identified. The early signature may reflect activation of the Unfolded Protein Response (ATF3 for instance), which is known to be activated rapidly in response to hypoxia. Cross-talk between oxygen and glucose metabolism via HIF1 have been reported (11, 15) as well as the protective role of IGF1 against cell degeneration in animal models after stroke such as hypoxia-ischemia (17).

Late Hypoxia

The late signatures (0% oxygen and 2% oxygen) were found to be very similar to the Chi signature, with an overlap for each one greater than 40% (and up to 70% with their short versions). The biological theme of the late signatures is also typical of a hypoxic response (6), with genes encoding proteins involved in the hypoxia pathway and angiogenesis (ANGPTL4, CA9, DDIT4, EGLN3, EGFR, HK2, HIG2, LOX); cell proliferation and apoptosis (BNIP3L, NDRG1, MXI1); glucose transport (many members of the solute carrier family including GLUT1); metabolism (ENO1, PGK1) and adrenomedullin (ADM). Similar to the four derived late hypoxia signatures, the Chi signature was found to be not significant in this data set. This suggests that late signatures are very similar to the Chi signature not only in gene content but also in terms of prognostic power.

Unsupervised and Supervised Hypoxia Signatures

Cluster analysis (7) is a commonly used technique (3, 10) to assess shared functions and common regulation in an unbiased way since the algorithm does not require user-defined (i.e. supervised) assumptions on the numbers nor type of clusters to be found. The underlying idea is that genes with a similar expression pattern are likely to also be involved in the same regulatory process (referred to as 'guilt by association'). This approach was used by Chi et al. to group temporal gene expression under hypoxia. From HMECs and RPTECs, one cluster of global up-regulated genes was then selected after visual inspection to form the 'epithelial cell hypoxia genes' or so-called Chi signature. The gene content of the early hypoxia signatures had virtually no overlap with the Chi signature: 2 UniGenes at 0% oxygen (Hs.149032, PIK3R4 and Hs.283749, RNASE4), and only 1 at 2% oxygen (Hs.94542, ALKBH1). This suggested that the early signatures are very different from the Chi signature.

Although external changes in milieu (e.g., hypoxia) are sensed very rapidly by the cell, large changes at the transcriptional level occur mostly after several hours. A supervised method was developed to extract a handful of genes involved in the early hypoxic response (i.e., from 1-6 hours of hypoxia). Overlap was seldom found between the early and the late signatures: only one UniGene at 0% oxygen (Hs.106861, NSD1), and none under 2% oxygen. It shows that early signatures are different from late signatures (including the Chi signature) both in gene content and in patients they select.

All early hypoxia signatures whether extracted under 0% oxygen, 2% oxygen or their overlap were found significant on the Miller data set. Focusing on the former for multivariate analyses confirmed its prognostic power. At this moment it is unclear why the early hypoxic signatures provide superior prognostic information in this dataset. It may reflect differential activation of hypoxia response pathways, but may also select patients with more aggressive tumors (more metastasis), resistance to treatment or both. Additional methods are currently being investigated to validate our early gene signatures such as in vitro experiments with RNAi to selectively downregulate gene products (e.g., TERT or IGF1R) or by further testing the gene signature on independent clinical data sets with distinct clinical features. This retrospective study could be useful In the field of radiotherapy and oncology by suggesting the need for a prospective clinical study providing clinical data together with microarray data and an independent measure of hypoxia (by Eppendorf electrodes or immunochemistry staining for instance).

CONCLUSION

This analysis shows that, consistently with our hypothesis, the early and late hypoxia responses are very different at the transcription level. In a relatively old cohort of patients with primary breast cancer treated by locoregional therapy and systemic adjuvant therapy, it was shown that early hypoxia signatures, but not late hypoxia responses, could correlate with survival differences. It suggests that gene signatures can provide a mean to select patients for individualized therapy.

TABLE 1

Clinical information for the 251 patients composing the validation set

| Characteristic | |
|---|---|
| No. of patients | 251 |
| Age - years | 62.1 ± 13.9 |
| Tumor stage - no. of patients (%) | |
| Stage I | 67 (26.7) |
| Stage II | 128 (51.0) |
| Stage III | 54 (21.5) |
| Tumor size - mm | 22.4 ± 12.5 |
| ER (estrogen receptor) status - no. of patients (%) | |
| positive | 213 (84.9) |
| negative | 34 (13.5) |
| Lymph node status - no. of patients (%) | |
| positive | 84 (33.5) |
| negative | 158 (62.9) |
| Progesterone receptor status - no. of patients (%) | |
| positive | 190 (75.7) |
| negative | 61 (24.3) |
| p53 status - no. of patients (%) | |
| positive | 58 (23.1) |
| negative | 193 (76.9) |

TABLE 2A

Early 0%

| # | UniGene | Symbol | corr. | max |
|---|---|---|---|---|
| 1 | Hs.592692 | | 0.95 | 1.59 |
| 2 | Hs.633514 | TIMP2 | 0.92 | 3.49 |
| 3 | Hs.127126 | CPEB4 | 0.91 | 1.80 |

TABLE 2A-continued

Early 0%

| # | UniGene | Symbol | corr. | max |
|---|---------|--------|-------|-----|
| 4 | Hs.334587 | RBPMS | 0.90 | 1.35 |
| 5 | Hs.648626 |  | 0.89 | 1.09 |
| 6 | Hs.646346 | GAS6 | 0.87 | 1.65 |
| 7 | Hs.584803 | ST3GAL1 | 0.87 | 1.45 |
| 8 | Hs.567495 | TRNT1 | 0.85 | 1.80 |
| 9 | Hs.651126 | DUSP3 | 0.85 | 1.50 |
| 10 | Hs.478746 | CENTB2 | 0.84 | 2.60 |
| 11 | Hs.72550 | HMMR | 0.83 | 1.81 |
| 12 | Hs.154276 | BACH1 | 0.83 | 1.18 |
| 13 | Hs.233568 | HIST1H2AL | 0.82 | 2.15 |
| 14 | Hs.106861 | NSD1 | 0.81 | 1.51 |
| 15 | Hs.414418 | BET1L | 0.80 | 3.41 |
| 16 | Hs.593565 |  | 0.80 | 4.08 |
| 17 | Hs.235116 | GRK6 | 0.79 | 1.94 |
| 18 | Hs.554791 | TP53I11 | 0.79 | 1.65 |
| 19 | Hs.226780 | OSTM1 | 0.79 | 1.86 |
| 20 | Hs.525549 | BTBD7 | 0.79 | 2.68 |
| 21 | Hs.536158 | PARG | 0.79 | 2.83 |
| 22 | Hs.438489 | ATP5S | 0.79 | 1.12 |
| 23 | Hs.643279 | EIF4EBP2 | 0.79 | 2.96 |
| 24 | Hs.189772 | CCT2 | 0.77 | 3.24 |
| 25 | Hs.78977 | PCSK1 | 0.76 | 2.18 |
| 26 | Hs.155983 | JMJD2A | 0.76 | 2.03 |
| 27 | Hs.612872 | TTLL5 | 0.76 | 2.23 |
| 28 | Hs.435933 | PHF10 | 0.76 | 1.55 |
| 29 | Hs.489603 | ATXN7L1 | 0.76 | 3.60 |
| 30 | Hs.128959 | PCF11 | 0.75 | 3.40 |
| 31 | Hs.335205 | SSH2 | 0.74 | 2.84 |
| 32 | Hs.146406 | NIT1 | 0.74 | 1.81 |
| 33 | Hs.596783 |  | 0.73 | 1.14 |
| 34 | Hs.512973 | PTPLAD1 | 0.73 | 1.71 |
| 35 | Hs.461030 | GFOD2 | 0.73 | 1.99 |
| 36 | Hs.149983 | PEX14 | 0.73 | 4.49 |
| 37 | Hs.464137 | ACOX1 | 0.73 | 2.21 |
| 38 | Hs.292524 | CCNH | 0.72 | 3.27 |
| 39 | Hs.283749 | RNASE4 | 0.71 | 1.74 |
| 40 | Hs.287362 | TLE3 | 0.71 | 4.38 |
| 41 | Hs.492203 | TERT | 0.71 | 1.20 |
| 42 | Hs.250693 | ZNF117 | 0.71 | 1.04 |
| 43 | Hs.593232 |  | 0.70 | 3.15 |
| 44 | Hs.590575 | GRM3 | 0.70 | 3.26 |
| 45 | Hs.428214 | MAML2 | 0.70 | 3.13 |
| 46 | Hs.523847 | IFI6 | 0.70 | 4.68 |
| 47 | Hs.533712 | RBM4 | 0.70 | 2.29 |
| 48 | Hs.44067 | C12orf53 | 0.69 | 1.69 |
| 49 | Hs.647072 | PRKAG2 | 0.68 | 1.59 |
| 50 | Hs.606472 |  | 0.68 | 3.93 |
| 51 | Hs.149032 | PIK3R4 | 0.68 | 1.21 |
| 52 | Hs.436705 | KIAA1219 | 0.68 | 2.10 |
| 53 | Hs.631539 | RAB4B | 0.67 | 2.42 |
| 54 | Hs.529353 | ACSS1 | 0.67 | 2.55 |
| 55 | Hs.592020 | IGF1R | 0.67 | 4.02 |
| 56 | Hs.642938 | IGFBP1 | 0.67 | 1.63 |
| 57 | Hs.631930 | LOC646450 | 0.67 | 2.42 |
| 58 | Hs.148907 | SLC5A12 | 0.66 | 5.14 |
| 59 | Hs.160556 | ACACA | 0.65 | 1.63 |
| 60 | Hs.126891 | IL22RA2 | 0.64 | 1.63 |
| 61 | Hs.124011 |  | 0.64 | 1.70 |
| 62 | Hs.524828 | ZNF664 | 0.64 | 3.12 |
| 63 | Hs.4779 | GATAD2B | 0.64 | 2.28 |
| 64 | Hs.612872 | TTLL5 | 0.63 | 1.63 |
| 65 | Hs.233240 | COL6A3 | 0.63 | 1.19 |
| 66 | Hs.445030 | RHOBTB3 | 0.63 | 3.76 |
| 67 | Hs.460 | ATF3 | 0.63 | 1.79 |
| 68 | Hs.112432 | AMH | 0.63 | 2.24 |
| 69 | Hs.544738 | LY86 | 0.63 | 3.32 |
| 70 | Hs.530941 | C12orf30 | 0.63 | 3.66 |
| 71 | Hs.180903 | NCAPH2 | 0.63 | 1.81 |
| 72 | Hs.76364 | AIF1 | 0.62 | 3.06 |
| 73 | Hs.43627 | SOX12 | 0.62 | 6.59 |
| 74 | Hs.643599 | PAPPA | 0.62 | 1.96 |
| 75 | Hs.125038 | FAM92A1 | 0.61 | 1.82 |
| 76 | Hs.131342 | CCL26 | 0.61 | 2.59 |
| 77 | Hs.512767 | DKFZP761H17 | 0.61 | 2.67 |
| 78 | Hs.631974 | LOC728488 | 0.60 | 1.31 |
| 79 | Hs.112873 | IGSF11 | 0.60 | 1.65 |
| 80 | Hs.6217 |  | 0.60 | 1.93 |

TABLE 2B

Late 0% short

| SEQ ID NO: | UniGene | Symbol | corr. | max |
|---|---------|--------|-------|-----|
| 102 | Hs.102267 | LOX | 1.00 | 1.26 |
| 103 | Hs.435051 | CDKN2D | 1.00 | 1.16 |
| 104 | Hs.520819 | INSIG1 | 0.99 | 2.18 |
| 105 | Hs.380906 | MYADM | 0.98 | 1.56 |
| 106 | Hs.102267 | LOX | 0.98 | 2.38 |
| 107 | Hs.523012 | DDIT4 | 0.98 | 1.69 |
| 108 | Hs.465870 | KEAP1 | 0.97 | 1.42 |
| 109 | Hs.649390 |  | 0.97 | 1.20 |
| 110 | Hs.173381 | DPYSL2 | 0.97 | 2.70 |
| 111 | Hs.287659 | STRBP | 0.97 | 2.70 |
| 112 | Hs.131433 | ADAMTS13 | 0.97 | 3.65 |
| 113 | Hs.443976 | CEP250 | 0.97 | 1.52 |
| 114 | Hs.235782 | SLCO4A1 | 0.96 | 2.24 |
| 115 | Hs.405662 | CRABP2 | 0.96 | 1.33 |
| 116 | Hs.34871 | ZFHX1B | 0.96 | 2.58 |
| 117 | Hs.269722 | TCBA1 | 0.96 | 1.65 |
| 118 | Hs.540696 | SLC6A8 | 0.96 | 3.26 |
| 119 | Hs.644065 | TSC22D2 | 0.96 | 1.43 |
| 120 | Hs.129003 |  | 0.95 | 2.49 |
| 121 | Hs.502116 | NAV2 | 0.95 | 2.02 |
| 122 | Hs.511915 | ENO2 | 0.95 | 4.10 |
| 123 | Hs.530381 | PIM3 | 0.95 | 2.03 |
| 124 | Hs.497822 | DUSP10 | 0.95 | 2.26 |
| 125 | Hs.379821 | FAM83A | 0.95 | 1.36 |
| 126 | Hs.96996 | HNRPAO | 0.95 | 2.50 |
| 127 | Hs.26010 | PFKP | 0.94 | 1.56 |
| 128 | Hs.75093 | PLOD1 | 0.94 | 2.01 |
| 129 | Hs.525704 | JUN | 0.93 | 2.15 |
| 130 | Hs.446240 | PRKCBP1 | 0.93 | 1.44 |
| 131 | Hs.89387 | CASC2 | 0.93 | 1.96 |
| 132 | Hs.288232 | SERINC5 | 0.93 | 1.03 |
| 133 | Hs.533887 | SMEK1 | 0.93 | 1.39 |
| 134 | Hs.78771 | PGK1 | 0.93 | 2.41 |
| 135 | Hs.108106 | UHRF1 | 0.93 | 1.46 |
| 136 | Hs.644649 |  | 0.93 | 3.49 |
| 137 | Hs.445402 | PCTK3 | 0.93 | 3.23 |
| 138 | Hs.535297 | ARID5B | 0.93 | 2.73 |
| 139 | Hs.515032 | MKNK2 | 0.92 | 2.76 |
| 140 | Hs.422113 | ZNF511 | 0.92 | 1.80 |
| 141 | Hs.133350 | CNOT2 | 0.92 | 2.65 |
| 142 | Hs.146688 | PTGES | 0.92 | 1.15 |
| 143 | Hs.460355 | PRKCB1 | 0.92 | 2.79 |
| 144 | Hs.369520 | SYTL2 | 0.92 | 4.32 |
| 145 | Hs.647120 | MLL3 | 0.92 | 4.44 |
| 146 | Hs.517145 | ENO1 | 0.92 | 1.62 |
| 147 | Hs.533782 | KRT8 | 0.91 | 1.83 |
| 148 | Hs.21681 | GPR75 | 0.91 | 1.55 |
| 149 | Hs.458513 | PPP1R3B | 0.91 | 2.57 |
| 150 | Hs.643452 | DGCR8 | 0.91 | 2.82 |
| 151 | Hs.591443 | RAVER2 | 0.91 | 1.14 |
| 152 | Hs.433146 | SLC6A10P | 0.91 | 3.62 |
| 153 | Hs.429879 | EHHADH | 0.91 | 4.21 |
| 154 | Hs.9613 | ANGPTL4 | 0.91 | 4.95 |
| 155 | Hs.494529 | FANCC | 0.91 | 1.94 |
| 156 | Hs.523012 | DDIT4 | 0.91 | 2.14 |
| 157 | Hs.97858 | KIF1B | 0.90 | 2.55 |
| 158 | Hs.581355 | EIF4E3 | 0.90 | 3.84 |
| 159 | Hs.530904 | CSRP2 | 0.90 | 1.32 |
| 160 | Hs.159430 | FNDC3B | 0.90 | 1.73 |
| 161 | Hs.435667 | USP34 | 0.90 | 1.93 |
| 162 | Hs.505172 | LOC645619 | 0.90 | 1.93 |
| 163 | Hs.446017 | WSB1 | 0.90 | 2.09 |
| 164 | Hs.470633 | PDK1 | 0.89 | 2.22 |
| 165 | Hs.501023 | MXI1 | 0.89 | 4.06 |

TABLE 2B-continued

Late 0% short

| SEQ ID NO: | UniGene | Symbol | corr. | max |
|---|---|---|---|---|
| 166 | Hs.501023 | MXI1 | 0.89 | 1.92 |
| 167 | Hs.46423 | HIST1H4C | 0.89 | 1.75 |
| 168 | Hs.433146 | SLC6A10P | 0.89 | 3.61 |
| 169 | Hs.591849 | C8orf4 | 0.89 | 2.18 |
| 170 | Hs.159195 | DOCK1 | 0.89 | 3.02 |
| 171 | Hs.372914 | NDRG1 | 0.89 | 5.68 |
| 172 | Hs.8004 | KALRN | 0.89 | 2.67 |
| 173 | Hs.523789 | TncRNA | 0.89 | 2.14 |
| 174 | Hs.634882 | ARL6IP1 | 0.88 | 2.39 |
| 175 | Hs.585433 | KIRREL | 0.88 | 2.60 |

TABLE 2C

Early 2%

| SEQ ID NO: | UniGene | Symbol | corr. | max |
|---|---|---|---|---|
| 11 | Hs.72550 | HMMR | 0.90 | 2.39 |
| 81 | Hs.528299 | HTATIP | 0.90 | 1.84 |
| 82 | Hs.510078 | SGK | 0.86 | 1.58 |
| 2 | Hs.633514 | TIMP2 | 0.86 | 3.83 |
| 83 | Hs.602706 | LOC645591 | 0.86 | 1.63 |
| 84 | Hs.642877 | MALAT1 | 0.85 | 2.46 |
| 43 | Hs.593232 |  | 0.84 | 3.25 |
| 33 | Hs.596783 |  | 0.82 | 1.59 |
| 85 | Hs.441113 | MAGEA6 | 0.80 | 1.06 |
| 36 | Hs.149983 | PEX14 | 0.79 | 4.42 |
| 86 | Hs.94542 | ALKBH1 | 0.79 | 1.18 |
| 12 | Hs.154276 | BACH1 | 0.77 | 2.12 |
| 24 | Hs.189772 | CCT2 | 0.77 | 4.09 |
| 68 | Hs.112432 | AMH | 0.76 | 2.54 |
| 74 | Hs.643599 | PAPPA | 0.74 | 1.51 |
| 87 | Hs.126774 | DTL | 0.74 | 1.76 |
| 32 | Hs.146406 | NIT1 | 0.73 | 2.04 |
| 88 | Hs.463838 | LOC440459 | 0.73 | 1.25 |
| 46 | Hs.523847 | IFI6 | 0.72 | 4.45 |
| 89 | Hs.46700 | ING1 | 0.72 | 1.08 |
| 90 | Hs.55131 | C3orf23 | 0.71 | 1.21 |
| 91 | Hs.558396 | SCD | 0.70 | 1.64 |
| 58 | Hs.148907 | SLC5A12 | 0.70 | 4.49 |
| 92 | Hs.643920 | C1GALT1C1 | 0.69 | 2.17 |
| 59 | Hs.160556 | ACACA | 0.67 | 1.78 |
| 93 | Hs.562083 | ICMT | 0.66 | 2.27 |
| 94 | Hs.515383 | LOC644242 | 0.66 | 4.93 |
| 95 | Hs.513430 | CDR2 | 0.65 | 2.10 |
| 26 | Hs.155983 | JMJD2A | 0.63 | 2.71 |
| 44 | Hs.590575 | GRM3 | 0.62 | 3.65 |
| 96 | Hs.632226 | ITGB4 | 0.62 | 1.49 |
| 97 | Hs.165607 | FLJ25416 | 0.62 | 1.02 |
| 98 | Hs.514033 | SPAG5 | 0.61 | 1.92 |
| 99 | Hs.632447 | WDR42A | 0.61 | 1.87 |
| 100 | Hs.89603 | MUC1 | 0.60 | 2.11 |
| 101 | Hs.434961 | ATXN1 | 0.60 | 2.34 |

TABLE 2D

Late 2% short

| SEQ ID NO: | UniGene | Symbol | corr. | max |
|---|---|---|---|---|
| 176 | Hs.446017 | WSB1 | 1.00 | 1.77 |
| 177 | Hs.370365 | HK1 | 1.00 | 1.13 |
| 178 | Hs.520819 | INSIG1 | 0.97 | 1.51 |
| 179 | Hs.405662 | CRABP2 | 0.96 | 2.02 |
| 180 | Hs.173705 | LOC401152 | 0.94 | 2.24 |
| 181 | Hs.644649 |  | 0.94 | 2.91 |
| 182 | Hs.446017 | WSB1 | 0.94 | 1.32 |
| 183 | Hs.511915 | ENO2 | 0.94 | 3.18 |
| 184 | Hs.474935 | SEMA4B | 0.94 | 2.40 |
| 185 | Hs.497822 | DUSP10 | 0.94 | 2.06 |
| 186 | Hs.335614 | SEC14L2 | 0.93 | 2.59 |

TABLE 2D-continued

Late 2% short

| SEQ ID NO: | UniGene | Symbol | corr. | max |
|---|---|---|---|---|
| 187 | Hs.102267 | LOX | 0.93 | 2.47 |
| 188 | Hs.287659 | STRBP | 0.93 | 1.78 |
| 189 | Hs.502116 | NAV2 | 0.91 | 1.82 |
| 190 | Hs.581021 | SIRPA | 0.91 | 1.08 |
| 191 | Hs.403933 | FBXO32 | 0.91 | 2.85 |
| 192 | Hs.500047 | P4HA1 | 0.91 | 2.97 |
| 193 | Hs.540696 | SLC6A8 | 0.90 | 2.43 |
| 194 | Hs.2795 | LDHA | 0.89 | 1.38 |
| 195 | Hs.9613 | ANGPTL4 | 0.89 | 3.64 |
| 196 | Hs.535297 | ARID5B | 0.89 | 2.28 |
| 197 | Hs.173381 | DPYSL2 | 0.89 | 2.19 |
| 198 | Hs.429879 | EHHADH | 0.89 | 2.88 |
| 199 | Hs.425144 | MTMR11 | 0.89 | 1.74 |
| 200 | Hs.98643 | RAP2B | 0.89 | 1.44 |
| 201 | Hs.34871 | ZFHX1B | 0.88 | 2.08 |
| 202 | Hs.591140 | FOXK2 | 0.88 | 2.09 |
| 203 | Hs.581355 | EIF4E3 | 0.87 | 2.15 |
| 204 | Hs.155247 | ALDOC | 0.87 | 1.38 |
| 205 | Hs.501023 | MXI1 | 0.87 | 2.77 |
| 206 | Hs.536075 |  | 0.87 | 1.41 |
| 207 | Hs.102267 | LOX | 0.86 | 1.79 |
| 208 | Hs.132513 | HSD17B12 | 0.86 | 3.51 |
| 209 | Hs.132342 | LPIN2 | 0.86 | 1.87 |

TABLE 2E

| SEQ ID NO: | UniGene | Symbol | corr. | max |
|---|---|---|---|---|
| 11 | Hs.72550 | HMMR | 0.90 | 2.39 |
| 2 | Hs.633514 | TIMP2 | 0.86 | 3.83 |
| 43 | Hs.593232 |  | 0.84 | 3.25 |
| 33 | Hs.596783 |  | 0.82 | 1.59 |
| 36 | Hs.149983 | PEX14 | 0.79 | 4.42 |
| 12 | Hs.154276 | BACH1 | 0.77 | 2.12 |
| 24 | Hs.189772 | CCT2 | 0.77 | 4.09 |
| 68 | Hs.112432 | AMH | 0.76 | 2.54 |
| 74 | Hs.643599 | PAPPA | 0.74 | 1.51 |
| 32 | Hs.146406 | NIT1 | 0.73 | 2.04 |
| 46 | Hs.523847 | IFI6 | 0.72 | 4.45 |
| 58 | Hs.148907 | SLC5A12 | 0.70 | 4.49 |
| 59 | Hs.160556 | ACACA | 0.67 | 1.78 |
| 26 | Hs.155983 | JMJD2A | 0.63 | 2.71 |
| 44 | Hs.590575 | GRM3 | 0.62 | 3.65 |

TABLE 3

Validation of the early hypoxia gene Signatures: statistical differences between Kaplan-Meier survival curves were assessed by computed mean p-values obtained from log-rank tests at 5 and 10 years. For each signature. its type, correlation coefficient (not applicable for the Chi study), number of reporters and number of unique UniGene cluster IDs are also given.

| Oxygen Concentration (%) | Hypoxia type | Corr. coeff. | # reporters | # unique Unigenes | p-value |
|---|---|---|---|---|---|
| 0 | early | 0.6 | 80 | 79 | 0.004 |
| 0 | late | 0.6 | 241 | 210 | 0.118 |
| 0 | late | 0.88 | 74 | 70 | 0.110 |
| 2 | early | 0.6 | 36 | 36 | 0.034 |
| 2 | late | 0.6 | 169 | 147 | 0.919 |
| 2 | late | 0.86 | 34 | 32 | 0.842 |
| 0&2 | Chi et al. | n.a. | 253 | 171 | 0.300 |
| 0&2 | early | 0.6 | 15 | 15 | 0.005 |
| 0&2 | Late | 0.6 | 93 | 93 | 0.240 |

TABLE 4

Gene Ontology provided by Ingenuity for the early signatures. For each one, the top 2 functions which correspond to the highest scores are shown, as well as the genes contributing to the score. The top function of early genes overlapping between 0% and 2% are also given.

| Oxygen Conc. | Top functions | Score | Focus Genes | Gene Symbols |
|---|---|---|---|---|
| 0% | Cellular Growth and Proliferation, Cellular Development, Connective Tissue Development and Function | 27 | 14 | AIF1, ATF3, BACH1, CCL26, COL6A3, GATAD2B, GRK6, IL22RA2, PARG, PCSK1, PEX14, PIK3R4, TERT, TP53I11 |
| 0% | Cellular Function and Maintenance, Cancer, Cell Cycle | 25 | 13 | ACACA, ACOX1, ACSS1, AMH, CCNH, CCT2, GRM3, HMMR, IFI6, IGF1R, LY86, PTPLAD1, TLE3 |
| 2% | Cellular Function and Maintenance, Cell Cycle, Cancer | 27 | 12 | ACACA, AMH, BACH1, CDR2, HTATIP, IFI6, ING1, ITGB4, PEX14, SCD, SGK, SPAG5 |
| 2% | Cellular Movement, Connective Tissue Development and Function, Cancer | 9 | 5 | CCT2, GRM3, HMMR, ICMT, MUC1 |
| 0% and 2% | Cancer, Tumor Morphology, Amino Acid Metabolism | 11 | 5 | ACACA, AMH, BACH1, CCT2, IFI6 |

REFERENCES (1) Bild et al. Linking oncogenic pathways with therapeutic opportunities. Nat Rev Cancer 2006:6:735-41.

(2) Bussink et al. Microenvironmental transformations by VEGF- and EGF-receptor inhibition and potential implications for responsiveness to radiotherapy. Radiother Oncol 2007:82: I0-7.

(3) Chang et al. Gene expression signature of fibroblast serum response predicts human cancer progression: similarities between tumors and wounds. PLoS Biol 2004:2:E7.

(4) Chi et al. Gene expression programs in response to hypoxia: cell type specificity and prognostic significance in human cancers. PLoS Med 2006:3:e47.

(5) Chung et al. Molecular portraits and the family tree or cancer. Nat Genet 2002; 32 Suppl: 533-40.

(6) Denko et al. Investigating hypoxic tumor physiology through gene expression patterns. Oncogene 2003:22:5907-14.

(7) Eisen et al. Cluster analysis and display or genome-wide expression patterns. Proc Natl Acad Sci USA 1998:95: 14863-8.

(8) Eriksen et al. Tumour hypoxia—a characteristic feature with a complex molecular background. Radiother Oncol 2006:81: 119-21.

(9) Huang et al. Gene expression phenotypes of oncogenic signaling pathways. Cell Cycle 2003; 2:415-7.

(10) Iyer et al. The transcriptional program in the response of human fibroblasts to serum. Science 1999:283:83-7.

(11) Kietzmann. et al. Signaling cross-talk between hypoxia and glucose via hypoxia-inducible factor 1 and glucose response elements. Biochem Phannacol 2002:64:903-11.

(12) Koritzinsky et al. The hypoxic proteome is influenced by gene-specific changes in mRNA translation. Radiother Oncol 2005:76: 177-86.

(13) Miller et al. An expression signature for p53 status in human breast cancer predicts mutation status, transcriptional effects, and patient survival. Proc Natl Acad Sci USA 2005:102:13550-5.

(14) Ramaswamy et al. Multiclass cancer diagnosis using tumor gene expression signatures. Proc Natl Acad Sci USA 200 I:98: 15149-54.

(15) Riedemann et al. IGF1R signalling and its inhibition. Endocr Relat Cancer 2006:13 Suppl I:S33-43.

(16) Sjogren et al. The p53 gene in breast cancer: prognostic value of complementary DNA sequencing versus immunohistochemistry. J Natl Cancer Inst 1996; 88: 173-82.

(17) Smith. Neuroprotection against hypoxia-ischemia by insulin-like growth factor-I (IGF-I). IDrugs 2003:6:1173-7.

(18) Sorensen et al. Influence or oxygen concentration and pH on expression of hypoxia induced genes. Radiother Oncol 2005:76: 187-93.

(19) Troost et al. Imaging hypoxia after oxygenation-modification: comparing [18F]FMISO autoradiography with pimonidazole immunohistochemistry in human xenograft tumors. Radiother Oncol 2006:80: 157-64.

(20) van't Veer et al. Gene expression profiling predicts clinical outcome of breast cancer. Nature 2002; 415: 530-6.

(21) van de Vijver et al. A gene-expression signature as a predictor of survival in breast cancer. N Engl J Med 2002: 347: 1999-2009.

(22) Vaupel. The role of hypoxia-induced factors in tumor progression. Oncologist 2004:9 Suppl 5: I0-7.

(23) Wouters et al. Targeting hypoxia tolerance in cancer. Drug Resist Update 2004:7:25-10.

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07960114B2). An electronic copy of the "Sequence Listing" will also be available from the USPTO upon request and payment of the fee set forth in 37 CFR 1.19(b)(3).

What is claimed:

1. A method for predicting a breast cancer patient response to chemotherapy comprising:

measuring in a breast cancer tissue sample from a breast cancer patient the levels of RNA expression of the polynucleotide sequences SEQ ID NOS: 11, 2, 43, 33, 36, 12, 24, 68, 74, 32, 46, 58, 59, 26, and 44, where an increase in the level of RNA expression predicts a favorable response to chemotherapy.

2. The method of claim 1, wherein said breast cancer tissue sample is from a tumor, a cancerous tissue, a pre-cancerous tissue, a biopsy, a tissue, lymph node, a surgical excision, blood, serum, urine, an organ, or saliva.

* * * * *